United States Patent [19]

Klicek

[11] Patent Number: 5,423,809
[45] Date of Patent: Jun. 13, 1995

[54] ELECTROSURGICAL CONTROL FOR A TROCAR

[75] Inventor: Michael S. Klicek, Boulder, Colo.

[73] Assignee: Valleylab Inc., Boulder, Colo.

[21] Appl. No.: 113,368

[22] Filed: Aug. 30, 1993

Related U.S. Application Data

[63] Continuation of Ser. No. 823,093, Jan. 21, 1992, abandoned.

[51] Int. Cl.[6] .............................................. A61B 17/36
[52] U.S. Cl. ....................................... 606/38; 606/45
[58] Field of Search ......................................... 606/3–7, 606/34–50; 604/272–274; 364/413.01,413.02; 607/62, 115

[56] References Cited

U.S. PATENT DOCUMENTS

| 3,601,126 | 1/1969 | Estes . | |
|---|---|---|---|
| 4,416,277 | 11/1983 | Newton et al. . | |
| 4,494,541 | 6/1985 | Archibald . | |
| 4,651,280 | 3/1987 | Chang et al. . | |
| 5,158,560 | 10/1992 | Sogawa et al. | 606/7 |
| 5,273,524 | 12/1993 | Fox et al. | 606/45 |

FOREIGN PATENT DOCUMENTS

3824913   2/1990  Germany .
2266245A  2/1993  United Kingdom .

Primary Examiner—William E. Kamm
Assistant Examiner—Marianne Parker
Attorney, Agent, or Firm—Peter C. Richardson; Lawrence C. Akers; Aaron Passman

[57] ABSTRACT

An electrosurgical control for a trocar has a trocar with a cannula with a stylet coaxially fit therein. The stylet is movable relative to the cannula along a common axis. The trocar is shaped for insertion in a direction generally along the axis through tissue in a puncture procedure with its stylet. A distal end and a proximal end on the elongate cannula so the distal end enters the tissue while the proximal end remains outside. A tip on the stylet end, near the distal end of the cannula, normally extends therebeyond in position to puncture the tissue. The stylet has an energy supply passing from the tip to its opposite end and moves reciprocally relative to the cannula so the tip extends or is fully within the cannula. An electrosurgical generator provides energy to the opposite end of the stylet and an electrosurgically active device is a part of the tip and connects to the energy supply. A sampling circuit connected to the electrosurgically active device and responds to changes in energy passing through the energy supply as a function of tissue cut by the electrosurgically active device. The sampling circuit provides a signal relative to the energy supplied and a measuring circuit analyzes the signal to instantly isolate a specific signal therefrom indicative of a significant change in the energy when the tip is not in tissue. A comparator has a settable predetermined threshold amount of energy at which the electrosurgical generator no longer supplies energy. A peak energy level is set by a knob and is compared to the varying signals from the sampling circuit. A switch responds to the comparator to disconnect the energy when the threshold is exceeded.

16 Claims, 5 Drawing Sheets

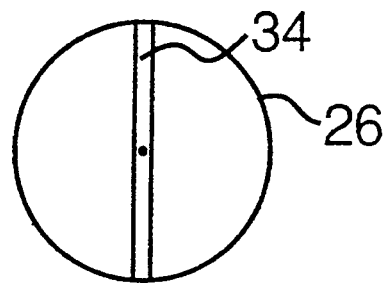
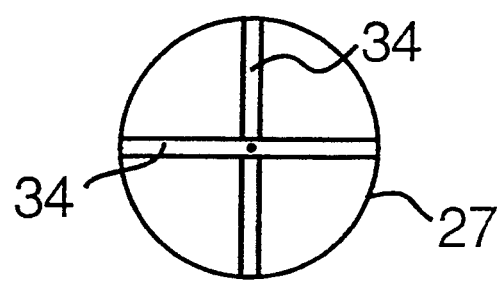
Figure 5a                Figure 5b
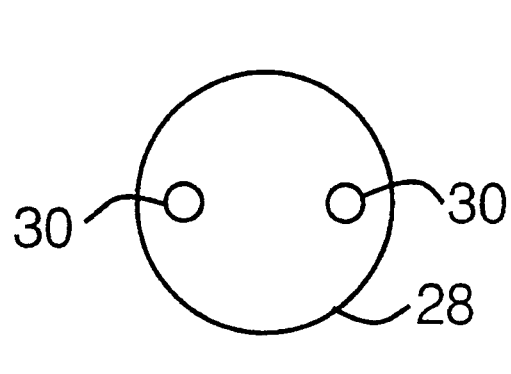
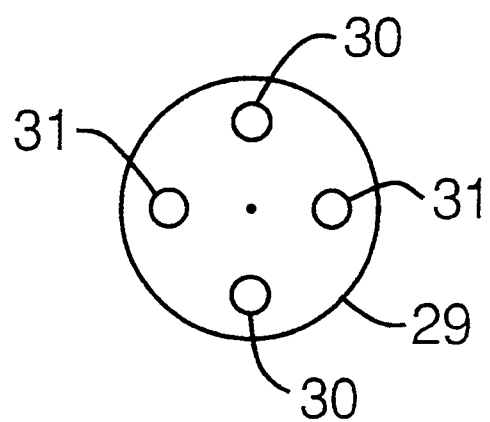
Figure 5c                Figure 5d

ELECTROSURGICAL CONTROL FOR A TROCAR

This is a continuation of application Ser. No. 07/823,093, filed on Jan. 21, 1992 now abandoned.

1. FIELD OF THE INVENTION

An electrosurgical generator control responsive to energy required to cut tissue of a human or animal, and more specifically the energy flowing through a distal tip of a cutting instrument applied directly to the tissue.

2. BACKGROUND OF THE DISCLOSURE

Surgery through a trocar inserted cannula and particularly with an opening through the tissue of an animal or human abdominal wall has become an important means to minimize the extent of surgical invasion. The lessening of invasion improves the cosmetic result, shortens recovery and lowers the cost. Endoscopic internal surgical procedures and equipment are available and in use for a variety of medical operations including gall bladder, bowel and gynecological surgery. A proper and simple instrument to open the passage through the abdominal wall and avoid injury to internal organs during the placement of the cannula by means of a trocar is needed.

U.S. Pat. No. 3,595,239 discloses a catheter tube having an obturator in the form of an electrode passing coaxially therethrough. The obturator electrode is connected to an electrosurgical generator in order to provide high frequency energy used to divide or cut tissue thereby forming a passage for the catheter to pass through. The tip of the obturator extends beyond the catheter tip and is capable of cutting. The catheter is moved along with the obturator electrode by means of a ring disposed about the obturator proximal to the tip and inside the tip of the catheter. There is no disclosure of any means for sensing the impedance or load associated with the energy required to do the cutting during insertion of the obturator tip.

U.S. Pat. No. 4,856,530 discloses an automatic system for determination of the size of a catheter distal tip remotely at the proximal end of the catheter. A capacitor at the distal tip is connected to a pair of wires which extends proximally to a microprocessor which determines the decay constant of the capacitor and thereby establishes the catheter size. There is no disclosure of interactive measurement of the energy required for cutting tissue by impedance load or otherwise.

U.S. Pat. No. 4,651,280 discloses a microprocessor with a preset control for an electrosurgical unit during a transurethral resection. A current monitoring probe about the output of the electrosurgical unit is responsive to load such that differences in the tissue and in inclusions therein are measured as changes in conductivity which are directly related to the load during the resection. Variation and output power of the electrosurgical unit are a measure of what tissue is resected. The current changes are sensed by a peak detector, connected to a phase shifter so that a control signal relative to the current level can be provided to a sample and hold circuit to accumulate data that can be converted by an analog to digital converter for processing by a microprocessor.

U.S. Pat. No. 3,601,126 teaches delivery of power at a constant level to the active electrode as it engages the tissue and during the entire operational procedure. A reference current amplitude is used to maintain the cutting current constant. There is no disclosure of monitoring the energy or preventing the increase of energy upon entry into an internal cavity of the body.

U.S. Pat. No. 4,126,137 has voltage and current sensors which are used to monitor power used during cutting. The circuit suggests that to make linear the power delivery at high and low impedance the power is increased and decreased, respectively. That is, with changes in impedance the power is increased with increasing impedance. There is no appreciation of the need to cut off power with increased impedance to provide safety.

U.S. Pat. No. 4,231,372 has a current sensor in series with the ground. A comparator sets a threshold at which an alarm or disabling circuit functions as the current exceeds the threshold. Reset of the operation is timed and automatic so there is no safety responsive to an impedance increase upon reaching an inner cavity of the body.

U.S. Pat. No. 4,232,676 has a knife blade which cuts and cauterizes the incision and in so doing self limits the current flow at the knife. Specifically, the blade has electrodes across which current flows when there is a conductive path after cutting the current cauterizes the incision sealing the wound and eliminating the current path. No recognition of the impedance change due to the inner cavity of the body is disclosed.

U.S. Pat. No. 4,281,373 has a circuit responsive to the needs of the cutting effort required. If the power is inadequate to prevent sticking of the cutter in the tissue the power is increased. There is no safety circuit responsive to the change in power required when the cutter has reached a body cavity.

U.S. Pat. No. 4,416,277 monitors the contact resistance of the return electrode maintaining the impedance within a range to prevent burns. Automatic setting of the upper limit as a function of load is taught so the power is regulated. There is an alert but no shut off when a body cavity is entered and high impedance is detected.

U.S. Pat. No. 4,494,541 senses capacitance between the body and an electrically conductive layer isolated from the body but part of the return electrode. If the capacitance is not within a certain range an alarm is produced. Although current to the active electrode may be stopped if an alarm condition is detected, it is not a function of having reached an internal cavity of the body.

U.S. Pat. No. 4,498,475 has an intensity controlled by changing resistance which controls a transistor that turns the power on and off. There is no detection of impedance change at the inner body cavity.

U.S. Pat. Nos. 4,601,710 and 4,654,030 teach trocar tubes with a shielding sleeve in addition to the tube. The shielding sleeve may project beyond the end of the trocar thereby shielding the tip of the trocar while in the body cavity.

U.S. Pat. No. 4,535,773 discloses techniques for shielding the sharp tip of a trocar by either interposing an extensible shielding sleeve or retracting the trocar into its tube. With regard to the latter, a solenoid operated detent holds the trocar in an extended position relative its tube and electronic sensing in the tip of the trocar is used to activate the detent for release. Nothing in this reference has any disclosure of an impedance responsible circuit used to regulate an electrosurgical generator, attached to an electrosurgical cutting tip. Sensors and switches are used in conjunction with the probe which retracts during penetration. In particular, the probe extends beyond the cutting surface once the abdominal wall has been traversed. The sensors can be connected to an oral or visual signal to indicate completion of the puncture. The switches could be mechanical or magnetic, be tripped by a sleeve in the puncturing instrument, a probe or a spring wire protruding from the tip or blade of a sharp pointed cutter. Multiple sensors in the cutting blade and the cannula can be used to signal circuit of the penetration position. No disclosure of an impedance sensitive circuit is in this rather extensive disclosure.

U.S. Pat. No. 4,919,653 discloses a device for locating epidural space. The release of force on the tip of a needle triggers an alarm which activate a solenoid latch permitting the needle and its sleeve to move in a cannula in response to an activated electromagnet such that the distal end moves 2 mm into the epidural space. Pressure sensors detect when the depression or release of pressure occurs as the needle enters the epidural space. The pressure signal is converted to produce the voltage difference between the sensor and the potentiometer. This difference is shown on a meter. The pressure sensor can be a small membrane with electrical contacts which are closed in the unloaded position and open when the membrane moves when the epidural space is reached. The passage of current through the contacts keeps the circuit open by means of a relay.

To safely place a cannula by a trocar technique requires knowledge of the position of the distal cutting tip of the stylet used to open the passage for the cannula through the animal or human tissue of the abdominal wall. A device to instant indicate when the cutting tip has passed through the tissue and reached the inside of the body is needed so that the internal organs are not injured. Because the organs fill the inside cavity and are close to the wall there is the possibility of injury before the surgeon can stop advancing the distal cutting tip.

SUMMARY OF THE DISCLOSURE

An electrosurgical control for a trocar preferably has a cannula with a stylet coaxially fit therewithin and the stylet is movable relative to the cannula along an axis common to both. The trocar is most preferably shaped for insertion in a direction generally along the axis through the tissue of a human or animal body in a combined puncture procedure with its stylet.

A distal end and a proximal end are preferably provided on the cannula. The cannula most preferably elongate so the distal end enters the tissue while the proximal end remains outside the tissue. A tip on the stylet end may first enter the tissue since the tip is preferably associated with the distal end of the cannula and normally extends therebeyond in position for puncture through the tissue, The stylet includes an energy supply therealong passing from the tip to an opposite end. The stylet is arranged to move reciprocally relative to the cannula for positioning the tip from its extended position to a location wherein the tip is fully within the cannula.

An electrosurgical generator provides energy to the energy supply at the opposite end of the stylet. An electrosurgically active device is preferably included as part of the tip and connects the energy supply of the stylet to the electrosurgical generator. A sampling circuit may be associated with the electrosurgically active device and is responsive to changes in energy passing through the energy supply as a function of tissue acted upon by the electrosurgically active device when as energized by the electrosurgical generator. The sampling circuit is most preferably for providing a signal relative to the energy supplied to the electrosurgically active device.

A measuring circuit may respond to and analyze the signal from the sampling circuit to instantly isolate a specific signal therefrom indicative of a significant change in the energy passing through the electrosurgically active device when the tip is not in tissue. A comparator includes a settable predetermined threshold amount of energy at which the electrosurgical generator no longer supplies energy to the electrosurgically active device.

The settable predetermined threshold is preferably a peak energy level as set by a knob adjusted by the electrosurgical control operator and the peak energy level is compared to the varying signals from the sampling circuit. A switch responsive to the comparator and connected to the electrosurgical generator may disconnect the energy supply therefrom when the threshold is exceeded. The comparator may operate the switch when a maximum or when a minimum is exceeded. The electrosurgically active device in circuit with the electrosurgical generator may form a monopolar system or a bipolar system. The bipolar system may include a pair of electrodes connected to the energy supply to the electrosurgically active device wherein the electrodes terminate and provide a site across which an arc of electrical energy can be sustained in circuit with the electrosurgical generator.

The sampling circuit may preferably respond to changes in voltage as the measure of energy flow through the energy supply and is a function of tissue acted upon by the electrosurgically active device at the tip of the stylet when energized by the electrosurgical generator. The sampling circuit provides a voltage relative to the energy supplied to the electrosurgically active device. The sampling circuit most preferably responds to changes in impedance of the tissue as the measure of energy required from the energy supply to the tip of the stylet when energized by the electrosurgical generator.

The electrosurgically active device at the tip of the stylet is most preferably a wire passing substantially normal to the axis of the cannula. The cannula is preferably cylindrical and may have a diameter thereacross and the stylet fits therein so the wire extends substantially across the diameter for cutting an opening through the tissue approximately the width of the cannula.

BRIEF DESCRIPTION OF THE DRAWINGS

FIGS. 5a through 5d include illustrations of the electrode designs shown in plan view for use as the electrosurgically active devices and in particular, FIG. 5a is a single cutting wire as shown in FIGS. 1 and 2; FIG. 5b has two crossing wires; FIG. 5c is an electrode with a pair of spaced apart active and sensing leads between which current flows during cutting, and FIG. 5d is an arrangement with two sensing leads and two active leads each pair spaced from each other and disposed normal to each other.

DETAILED DESCRIPTION OF THE DRAWINGS

Figure 1:
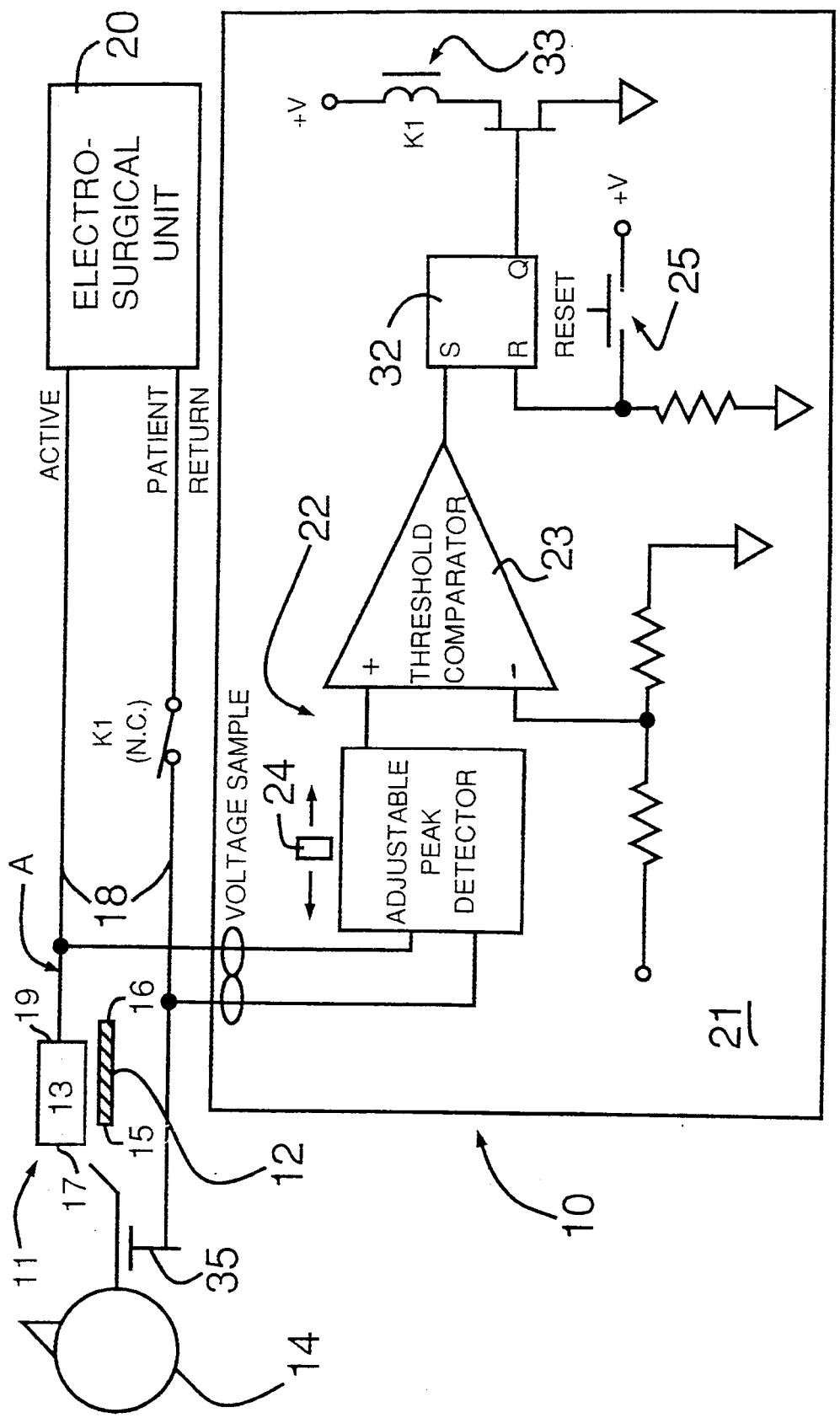
FIG. 1 is a schematic illustration of an electrosurgical control for a trocar with blocks to show the relationship of the circuit components of the preferred embodiment.

FIG. 1 is a schematic illustration of an electrosurgical control 10 showing the preferred embodiment as applied to a human during an electrosurgical procedure. The schematic blocks in FIG. 1 illustrate the relationship of the circuit components of the preferred embodiment. Specifically, an electrosurgical control 10 for a trocar 11 preferably has a cannula 12 with a stylet 13 coaxially fit therewithin and the stylet 13 is movable relative to the cannula 12 along an axis common to both.

The trocar 11 is shaped for insertion in a direction generally along the axis through the tissue of a human or animal body 14 and in FIG. 1 a human body is represented schematically. The preferred procedure is a combined puncture procedure wherein the cannula 12 is passed through a cut down incision with its stylet 13 whereby the opening through the abdominal wall is enlarged to be about 10 mm in diameter so an endoscope, laparoscopy or other observational or surgical instruments may have access to the internal organs.

Since many medical procedures access the inside of an anatomical cavity by using an implement such as a trocar 11, cannula 12 or needle having a sharpened point to pierce or puncture the bodily tissues, muscles and membranes forming the cavity wall. A surgical needle, for example, connected to a catheter is typically used to pierce a cavity (blood vessel, subarachnoid space, heart ventricle). After piercing the cavity, the needle is left in situ and used to inject or withdraw gaseous or liquid phase fluids from the cavity. Similarly, in several endoscopic procedures, a small incision may be made in the skin of a patient along the abdomen for example, and the sharp point of a larger penetrating implement such as a trocar of suitable length and diameter is inserted into the incision, and pushed until the point punctures the cavity wall. Then, a sleeve is slid over the exterior surface of the implement into the puncture wound to serve as a lining for preserving the shape of the passageway created by the implement. After the sleeve is in place and the implement is withdrawn, an endoscope and/or operating instruments may be inserted through the sleeve to view and/or operate upon organs within the cavity.

Although penetrating the wall of an anatomical cavity with a surgical puncturing instrument can be quickly done creating a small neat passageway and providing communication to the interior of the cavity, the sharp point of a penetrating implement pushed through a cavity wall may encounter great resistance from the tissue, muscle and membranes forming the cavity wall. When the sharp point and blade of the implement has passed through the cavity wall and into the cavity, the resistance drops significantly. The sharp point of the implement, however, can easily injure organ structure upon the slightest contact. Unless a surgeon stops pushing the implement just as soon as penetration is complete, there is a grave risk that the implement will continue penetrating deeply into the cavity and injure neighboring organ structure. If an unintended bodily member is injured by the point of the implement, unless an immediate and massive hemorrhage occurs, the injury may not become apparent until long after completion of the surgery. At a minimum, such an injury will delay a patient's recovery and may seriously endanger the patient's health and corrective surgery may be required.

Use of electrosurgery to cut through the wall if controlled automatically can prevent the unintended injury since the cutting may be monitored and controlled externally near or at the source of the energy supply. Moreover the energy to the electrosurgical cutter may by terminated when it is not in tissue. The preferred control and various electrosurgical cutters are described by way of example and are not disclosed to limit the coverage in the claims.

A trocar having a cannula and a stylet. A distal end 15 and a proximal end 16 are preferably provided on the cannula 12 in accord with FIG. 1. The cannula 12 is elongate so the distal end 15 enters the tissue while the proximal end 16 remains outside the tissue. A tip 17 on the stylet 15 enters the tissue first since the tip 17 is preferably associated with the distal end 15 of the cannula 12 and normally extends therebeyond, as shown in FIG. 4, in position for electrosurgically cut through the tissue. The stylet 13 includes an energy supply 18 therealong passing from the tip 17 to an opposite end 19. The stylet 13 is arranged to move reciprocally relative to the cannula 12 for positioning the tip 17 from its extended position to a location wherein the tip 17 is fully within the cannula 12; axial stylet movement is suggested by the arrows of FIGS. 3 and 4.

An electrosurgical generator 20 as shown schematically in block form in FIG. 1 could be a Model Force 2 as manufactured and sold by Valley Lab Inc. of Boulder, Colo. The electrosurgical generator 20 provides energy to the energy supply 18 at the opposite end 19 of the stylet 13. An electrosurgically active device may take many forms as will be described herein and is preferably included as part of the tip 17 and connects or completes the circuit between the energy supply 18 of the stylet 13 and the electrosurgical generator 20 by a monopolar or bipolar configuration. The electrosurgically active device used in conjunction with the trocar 11 leads to certain safety concerns. While the electrosurgically active device removes or at least reduces the force required to penetrate the patient's tissue it does not eliminate the danger of contacting internal organs and/or causing electrosurgical burns. Arcing or sparking caused by the energy jumping to other internal parts of the patient is of concern since contact with the electrosurgically active device is not required for that to occur.

The electrosurgical control 10 includes a sampling circuit 21 associated with the electrosurgically active device which responds to changes in energy passing through the energy supply 18 as a function of tissue acted upon by the electrosurgically active device when as energized by the electrosurgical generator 20. The electrosurgical stylet 13 may cause internal damage if the doctor continues to advance or press the device into the patient while the surgeon is unaware of the fact that the flesh/fat/muscle layer has been penetrated. Physically contacting internal organs the electrosurgical current will cut or burn them. If the voltage supplied to the electrosurgically active device is sufficiently high, after penetration of the flesh/fat/muscle layer sparks emitted from the cutting loop of the device could deliver coagulation type damage to the patient's internal organs. This injury would have been administered unintentionally.

Therefore, a safety circuit associated with the electrosurgically active device must account for both unintentional contact and non-contact damage to internal organs. The safety circuit 21 should allow the insertion of the trocar 11 into the patient with minimal probability of internal organ damage. The sampling circuit 21 preferably provides a signal relative to the energy supplied to the electrosurgically active device during entry through the incision. A measuring circuit 22 analyzes the signal from the sampling circuit 21 to instantly isolate a specific signal therefrom indicative of a significant change in the energy passing through the electrosurgically active device. A comparator 23 includes a settable predetermined threshold amount of energy at which the electrosurgical generator 20 no longer supplies energy to the electrosurgically active device.

The settable predetermined threshold is preferably a peak energy level as set by a knob 24 adjusted by the electrosurgical control operator and the peak energy level is compared to the varying signals from the sampling circuit. A switch 25 responsive to the comparator 23 and connected to the electrosurgical generator 20 may disconnect the energy supply 18 therefrom when the threshold is exceeded. The comparator 23 operates the switch 25 when a maximum or when a minimum signal is exceeded.

The electrosurgically active device in circuit with the electrosurgical generator 20 may form a monopolar system 26 or a bipolar system 26. The bipolar system 28 may include a pair of electrodes 30 connected to the energy supply to the electrosurgically active device wherein the electrodes terminate and provide a site across which an arc of electrical energy can be sustained in circuit with the electrosurgical generator.

The sampling circuit 21 may respond to changes in voltage as the measure of energy flow through the energy supply 18 and is a function of tissue acted upon by the electrosurgically active device at the tip 17 of the stylet 13 when energized by the electrosurgical generator 20. The sampling circuit 21 provides a voltage relative to the energy supplied to the electrosurgically active device. The sampling circuit 21 preferably responds to changes in impedance of the tissue as the measure of energy required from the energy supply 18 to the tip 17 of the stylet 13 when energized by the electrosurgical generator 20.

While the block diagram of FIG. 1 is for a circuit design external to the generator 20, a circuit internal to the generator 20 is also possible. If voltage is the monitored signal, the initial voltage level upon contact to the outer layer of skin will be relatively high, once the skin muscle layer is entered the voltage will drop, and the voltage will rise again when the fat layer is passed through but before organs are contacted. This voltage level will be the maximum peak value for the generator power level. The peak detector will monitor the voltage wave form and through the use of a sample hold and bleed resistor maintain a value proportional to the peak voltage that the generator has delivered.

This signal will be delivered to the threshold comparator 23 which has its trip level set at the peak output voltage of the generator 20 as a function of the front panel power set point. When the threshold is reached the output of the comparator 23 will go high. The transition of the comparator 23 output from low to high will set the flip flop 32 indicating that maximum voltage has been obtained. The output of this flip flop 32 will energize a relay 33 which will open the patient return continuity and cause an alarm (if the circuit is external to a generator 20). A manual reset will allow the surgeon to continue tissue penetration if he deems more depth (trocar penetration) is required.

If the circuit is internal to the generator under control a more elaborate scheme can be used where a special mode of the generator 20 is designed for trocar insertion and the signals are monitored internal to the generator. The interruption of power can then be through the primary control circuitry of the generator rather than through the external means of a patient continuity monitor.

If current is the feedback signal then the peak detector 24 is actually looking for a minimum level of current to indicate that the probe tip is not in contact with tissue. The magnitude of the current signal will be the opposite of that of the voltage signal. The rest of the circuit will operate in a similar manner with the peak detector 24 set at a minimal current level to indicate a high impedance (i.e. air) load on the generator 20.

The peak detector 24 will actually be a minimum level detector and the polarity of the comparator 23 will be the opposite of that shown. If power is the feedback signal, then the output power of the generator 20 is monitored and when it reaches a near zero level (e.g. no load on the electrode tip) then the comparator 24 is fired. Its respective output levels are similar to current assuming that no internal feedback loops are regulating the output power as a function of generator load. The peak detector 24 and comparator 23 polarity are similar to that described for the current monitoring circuit.

Figure 3:
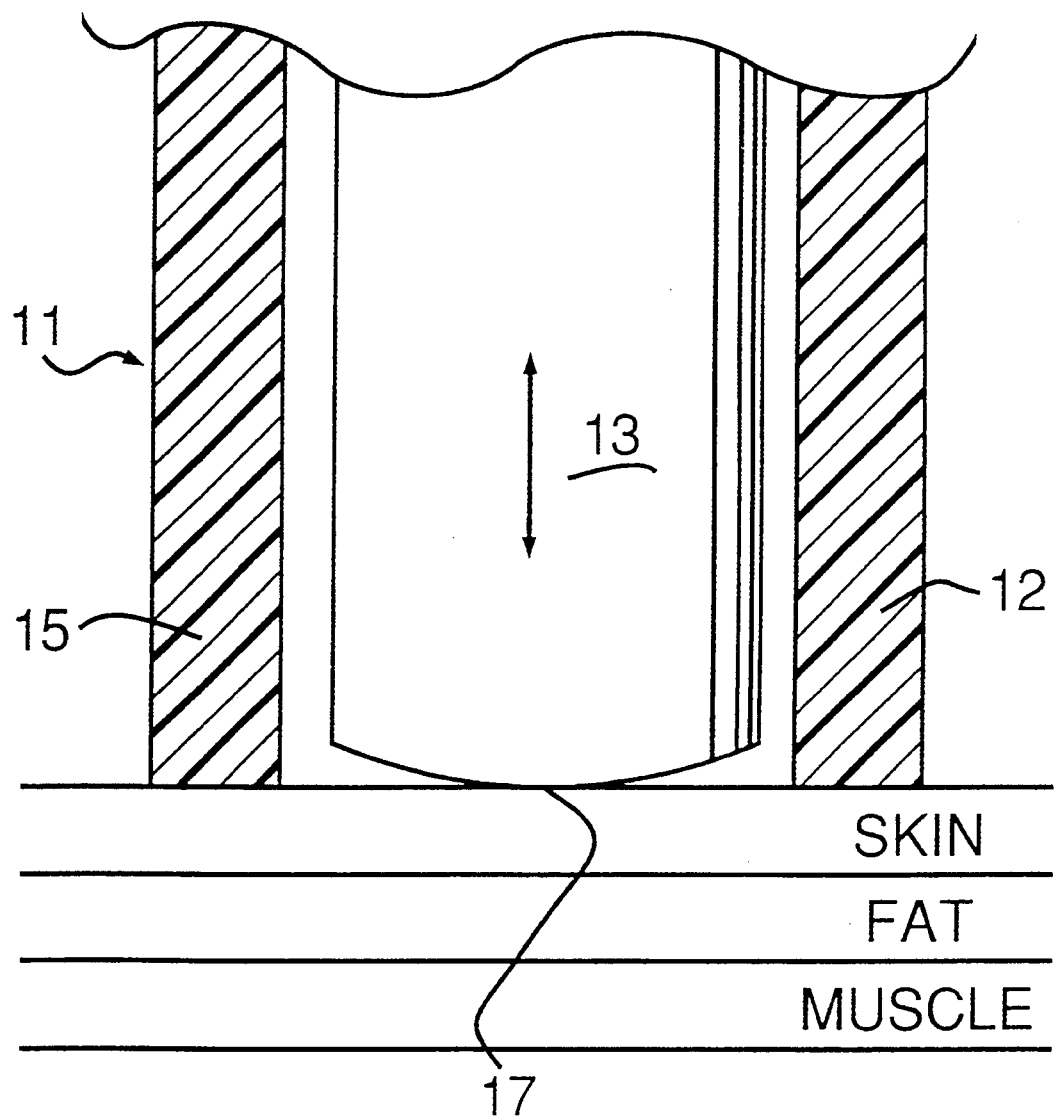
FIG. 3 is an enlarged illustration in cross section of the distal end of the trocar including the cannula and its stylet therewithin shown applied to the surface of the skin.
Figure 4:
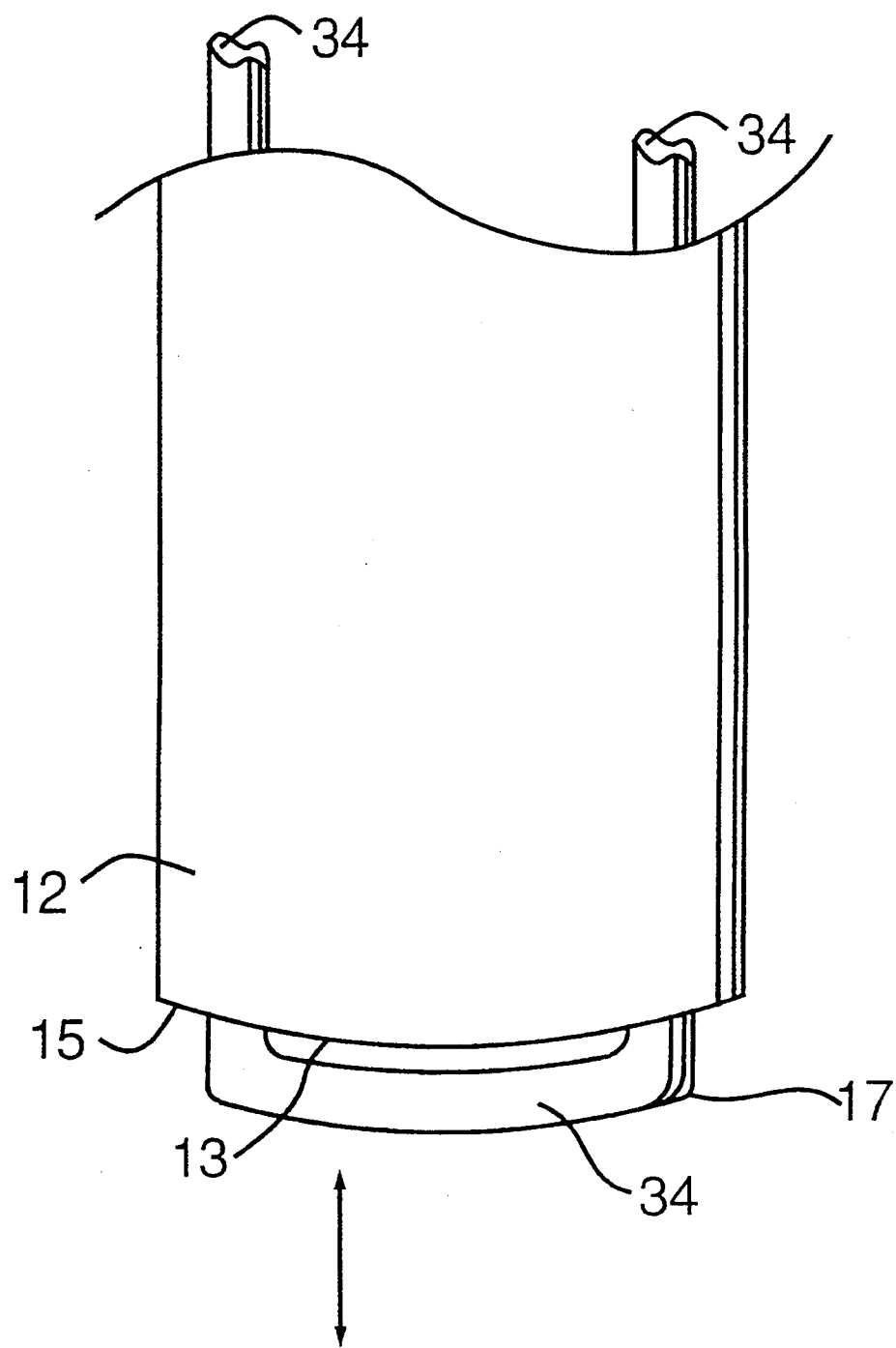
FIG. 4 is an enlarged illustration of the cannula and stylet wherein the stylet and a wire across the tip thereof is exposed or extended beyond the distal end of the cannula in position for use as the electrosurgically active device.

The electrosurgically active device at the tip 17 of the stylet 13 is preferably a wire 28 passing substantially normal to the axis of the cannula 12 as shown in FIGS. 3, 4, 5a and perhaps 5b. The cannula 12 is preferably cylindrical with a diameter thereacross so the stylet 13 fits therein. The wire 34 extends substantially across the diameter for cutting an opening through the tissue approximately the width of the cannula 12.

Figure 2:
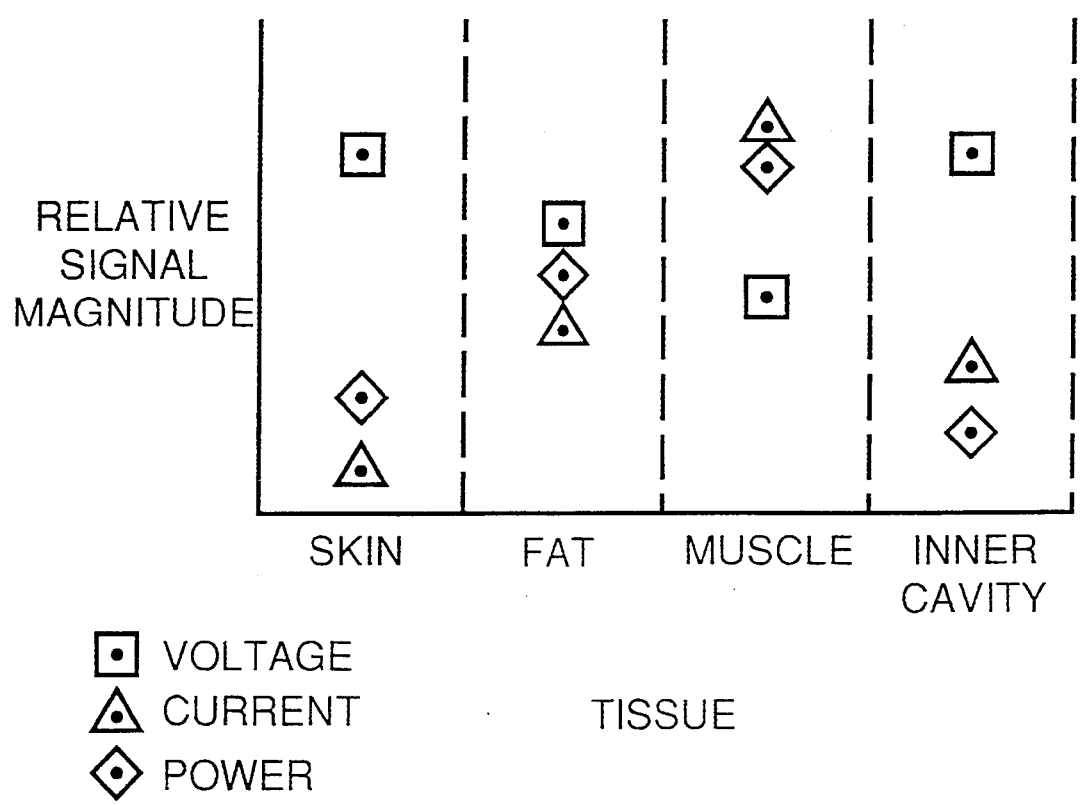
FIG. 2 is a plot showing graphically the change in energy required to cut as a function of the type of tissue in the abdominal wall of a human and specifically the tissue found between the skin and inner cavity.

The physical topology of the flesh/fat/muscle layer that must be penetrated is a variable in thickness and impedance range from patient to patient. FIG. 2 is a graphical depiction of different energy parameters relative to the constituents of the abdominal wall and includes a showing of the relationship of electrosurgical energy with respect to the tissue cut. Assuming that there is a small but finite cavity between the muscle layer and the internal organs, then automatic energy control is possible. The space could be assured by insufflation, inflating the abdominal cavity before application of the trocar 11.

Assuming that the device is monopolar in nature, that is only the electrosurgically active device is at the incision site and a patient return electrode is used as the return path for the cutting energy of the electrosurgically active device as suggested by FIG. 1. The safety circuit 21 must be able to hold the active voltage to a minimum to achieve a sufficiently efficacious cutting performance while reducing the potential sparking between the electrosurgically active device and the return path. A voltage of approximately 300 Volts may be adequate when combined with the mechanical design of the electrode to reduce the potential for sparking. That is the electrode could be slightly retracted into a nonconductive medium such as the cannula made of a high dielectric material. With a recessed stylet tip 17 the distal end of the cannula must be pressed gently into the tissue for the electrosurgically active device to cut.

The physical shape of the electrosurgically active device may be selected to be effective in reducing the potential for sparking and FIGS. 5a through 5d disclose various monopolar and bipolar arrangements. The surgically active device could be a point but the potential for sparking is increased as the probability of non contact increases as the electrode area is reduced. Conversely, the shape of the tip 17 could have a large cross sectional area which reduces the probability of non contact. However, the amount of energy required to perform cutting will increase as the size of the electrode increases. The amount of tissue damage that can occur is also directly proportional to the power setting of the generator 20. Therefore, increased tip size has negative impact.

The electrode is preferably disposable to minimize cost, the optimal design would be to use bipolar cutting electrodes as the sensing electrodes for tissue impedance, voltage, and/or current levels being delivered.

A monopolar needle electrode would achieve making a slender penetration hold to be mechanically distended as the trocar is inserted. A larger needle would obviously make a larger diameter hole thus reducing the overall distension required during trocar insertion. Voltage control, mechanical motion reduction, and penetration monitoring would be advisable for this configuration.

A monopolar loop would achieve making a much larger hole with a core of tissue having to be removed. The control parameters are the same as above. A wire type electrode could make a slot in the tissue similar to monopolar electrode. The control parameters are the same as above. A cross hairs type monopolar electrode would ideally create a four section 'flap' which would facilitate easier trocar insertion. The control parameters are the same as above.

A bipolar electrode would consist of two electrodes 30. The two electrodes 30 could be similar in size or vary in size to physically define one as the active electrode 30 (the smaller) and one as the return electrode 30. A coating on the electrodes 30 could also achieve the same effect. The two electrodes 30 could be shaped as to penetrate the flesh/fat/muscle layer in a coring fashion or in very close proximity to achieve a similar effect as a needle's electrode.

If the bipolar electrodes 30 are dissimilar in size by physically rotating them as they are inserted through the tissue even cutting or coring action can be achieved. The impedance of the tissue that is in contact with the electrode should be monitored. There are two ways of doing this:
  a. adding an auxiliary measurement circuit either to the "primary" active electrode(s) or a separate dedicated pair whose AC frequency is not a multiple of the fundamental operating frequency of the generator being used so that minimal "cross talk" between the auxiliary measurement current and the primary operating frequency of the generator occurs.
  b. monitoring the output voltage and current of the generator and using that information for calculating the tissue impedance which may be compared to a preset maximum.

Assuming that the impedance of the tissue that is encountered by the electrosurgically active device changes as it is inserted into the patient's body, then either monitoring the impedance or the first derivative of the impedance may detect the fact that the tip 17 of the stylet 13 has penetrated the flesh/fat/muscle layer. That is, entered the inner cavity. This concept is consistent with the data of FIG. 2. If there is a small void or cavity within the external layer and the internal organs, the electrosurgical control circuit 10 can detect the abrupt change (increase) in impedance and shut the electrosurgical generator 20 off.

If the device is bipolar in configuration it could be inherently safer than a monopolar electrosurgically active device. The potential for sparking to internal organs is reduced as the electrosurgical generator 20 output will be confined between the two electrodes 30 that are in close proximity to each other; see for example FIGS. 5c and 5d. The possibility for over inserting the device and damaging the internal organs still exists. Impedance monitoring would still be necessary to check for this misuse.

The optimal design might have a control that is bipolar. The device need not be driven from the bipolar output of an electrosurgical generator 20 as a true bipolar cut has yet to be achieved but rather the device can be connected to the monopolar stage of an electrosurgical generator 20 in a bipolar configuration. This will reduce the potential for sparking to internal organs once penetration has occurred. The trocar could be powered with a monopolar electrosurgical generator configured in the bipolar mode. The power level required to perform the trocar 11 entry would be a function of the bipolar electrode configuration (size, spacing, etc.) and, as explained elsewhere, has an active electrode and patient return 35 is connected to the other electrode of the device. The electrodes 30 should be as close as possible together so a coring action would result from its use. If a small diameter hole is achieved then the electrode body can be used to expand the hole through tissue flexibility. The trocar can be blunt and slowly inserted to avoid tissue damage at this point.

If the device had the mechanical means to allow slow entry of the electrode into the patient the probability of internal organ damage might be further reduced. This could easily be achieved if a simple reducing mechanism were used so that as the surgeon either turned a knob or dial, the electrode was slowly passed through the tissue layer. If the doctor has the capability of approximating the depth of the flesh/fat/muscle layer and a simple micrometer measurement device (e.g. markings on a wheel) could be used to determine when penetration is complete. A rotational to linear motion could be used for example with an associated reduction in motion. This would be ideal if the linear motion were derived from a rotation motion (e.g. the slow threading of the electrode into the patient). The depth of the flesh/fat/muscle layer could be measurable with a pair of micrometers. These device concepts could be used in conjunction with an impedance, current, and/or voltage monitoring control.

The monitoring of impedance can be done either by the electrosurgically active device performing the cutting or a pair or other combination of electrodes 30 attached to the tip 17 of the stylet 13. The monitoring circuit would interrogate the impedance by means of an AC electrical current and either look for an absolute value in either voltage or current, or would calculate impedance and monitor for an absolute impedance level or a change in the impedance. An absolute limit would be set an an impedance slightly greater than fat tissue to deactivate the generator while a change in impedance trip would be set for the impedance transition after the skin/fat muscle layer is penetrated.

If the control were a connected to an electrosurgical generator with a safety on the return electrode 35, the electrosurgical generator 20 could be deactivated at its return electrode by opening the return path. Once this circuit was interrupted, a physical action on the part of the practitioner (e.g. press a reset button 25) would be required to reactivate the generator 20. A patient alarm signal could be used to signal that the inner cavity has detected or that penetration has occurred.

If an external control is used as a measuring and control circuit for the trocar insertion device, it would be attached to the generator 20 when the trocar is being inserted and removed after insertion has occurred.

A predefined parameter would be electrically monitored for sensing that penetration has occurred i.e. entry to the inner cavity and would shut the generator off. A mechanical resetting action of the part of the practitioner would be required to continue using the device.

An ultrasonic tip may also be used to achieve tissue penetration. This could be indicated by mechanical depth, tissue selectivity using cavi-pulse, or an electronic control—of impedance. The measurement electrodes for impedance could be either part of the ultrasonic tip or separate attachments. An ultrasonic device would add the capabilities of electrosurgery to this type of device. Automatic shut off the ultrasonic and/or electrosurgical generator could be achieved via the use of monitoring electronic. The electrosurgical generator could deactivate the patient return electrode path and the ultrasonic generator could be manually shut off with the handswitch control being connected through the electronic monitor for deactivating the "on" signal.

It should be noted that any electrode tip, whether purely ultrasonic or electrosurgical or a combination of the two technologies, should be as blunt as possible to minimize any mechanical puncturing of tissue and to allow the maximum amount of penetration to be achieved by the respective cutting mechanism of the modality.

What is claimed is:

1. An electrosurgical control for a trocar comprising:
   a trocar having a stylet and a cannula coaxially fit to one another and the stylet is movable reciprocally relative to the cannula along an axis common to both, the trocar shaped for insertion in a direction generally along the axis through tissue of a human or animal body in a combined puncture procedure with its stylet;
   a distal end and a proximal end on the cannula, the cannula elongate between the ends thereof, the distal end for entering the tissue and the proximal end for remaining outside the tissue;
   a tip on the stylet end which enters the tissue, the tip associated with the distal end of the cannula and normally extending therebeyond in position for puncture through the tissue of a human or animal, the stylet having an end opposite the tip, the stylet arranged to be moveable relative to the cannula for positioning the tip in the extended position to a location with the tip fully within the cannula;
   an energy supply associated with the stylet for permitting passage of energy between the tip and the end opposite the tip;
   an electrosurgical generator connected to the energy supply for providing energy to the energy supply, the electrosurgical generator for connecting to the end opposite the tip of the stylet;
   an electrosurgically active device as part of the tip for connecting to the energy supply along the stylet;
   a sampling circuit associated with the electrosurgically active device responsive to changes in energy through the energy supply as a function of tissue acted upon by the electrosurgically active device at the tip of the stylet and as energized by the energy supply, the sampling circuit in a circuit with the energy supply and the electrosurgically active device for providing a signal relative to the energy supplied to the electrosurgically active device;
   a measuring circuit means connected to the sampling circuit to respond to and for analyzing the signal from the sampling circuit, the measuring circuit means for instantly isolating a specific signal therefrom indicative of a significant change in the energy passing through the electrosurgically active device when the tip thereof is in a body cavity and no longer in the tissue, and
   a comparator connected to the measuring circuit means, the comparator including a settable predetermined threshold amount of energy at which the electrosurgical generator no longer supplies energy to the electrosurgically active device when comparator relates the specific signal indicative of a significant change in the energy passing through the electrosurgically active device to the settable predetermined threshold amount of energy.

2. The electrosurgical control for a trocar of claim 1 wherein the settable predetermined threshold amount of energy is a peak energy level as set by a knob on the electrosurgical generator adjusted by the operator so the peak energy level is compared to the varying signals from the sampling circuit.

3. The electrosurgical control for a trocar of claim 1 wherein a switch responsive to the comparator and connected to the electrosurgical generator disconnects the energy supply therefrom when the threshold is exceeded.

4. The electrosurgical control for a trocar of claim 3 wherein the comparator operates the switch when a maximum is exceeded.

5. The electrosurgical control for a trocar of claim 3 wherein the comparator operates the switch when a minimum is exceeded.

6. The electrosurgical control for a trocar of claim 1 wherein the electrosurgically active device in circuit with the electrosurgical generator form a monopolar system.

7. The electrosurgical control for a trocar of claim 1 wherein the electrosurgically active device in circuit with the electrosurgical generator form a bipolar system.

8. The electrosurgical control for a trocar of claim 7 wherein the bipolar system includes a pair of electrodes connected to the energy supply to the electrosurgically active device wherein the electrodes terminate an provide a site across which an arc of electrical energy can be sustained in circuit with the electrosurgical generator.

9. The electrosurgical control for a trocar of claim 1 wherein the sampling circuit responds to changes in voltage is the measure of energy flow through the energy supply as a function of tissue acted upon by the electrosurgically active device at the tip of the stylet when energized by the electrosurgical generator, the sampling circuit for providing a voltage relative to the energy supplied to the electrosurgically active device.

10. The electrosurgical control for a trocar of claim 1 wherein the sampling circuit responds to changes in impedance of the tissue as the measure of energy required from the energy supply to the tip of the stylet when energized by the electrosurgical generator.

11. The electrosurgical control for a trocar for use with the cannula of claim 1 wherein the electrosurgically active device at the tip of the stylet is a wire passing substantially normal to the axis of the cannula.

12. The electrosurgical control for a trocar of claim 11 wherein the cannula is cylindrical and has a diameter thereacross and the stylet that fits therein has the wire extending across the diameter for cutting an opening through the tissue approximately the diameter of the cannula.

13. An electrosurgical control comprising:
an electrosurgically active device for an electrosurgical procedure for cutting an animal or human tissue wherein high frequency energy passes thereacross;
an electrosurgical generator for providing high frequency energy to the active device;
a sampling circuit associated with the electrosurgically active device responsive to changes in energy supplied therethrough as a function of tissue acted upon by the electrosurgically active device and as energized by the electrosurgical generator, the sampling circuit for providing a signal relative to energy supplied to the electrosurgically active device;
a measuring circuit means connected to the sampling circuit to respond thereto and for analyzing the signal from the sampling circuit, the measuring circuit means for instantly isolating a specific signal therefrom indicative of a significant change in energy passing through the electrosurgically active device as a consequence of the tip being no longer in the tissue, and
a comparator connected to the measuring circuit means, the comparator including a settable predetermined threshold amount of energy at which the electrosurgical generator no longer supplies energy to the electrosurgically active device.

14. The electrosurgical control of claim 13 wherein the sampling circuit provides the signal indicative of an increase in the energy passing through the electrosurgically active device as a consequence of the tip being beyond the tissue.

15. The electrosurgical control of claim 13 wherein the sampling circuit provides the signal indicative of a decrease in the energy passing through the electrosurgically active device as a consequence of the tip being beyond the tissue.

16. The electrosurgical control of claim 13 wherein the sampling circuit provides the signal indicative of the tip having passed through an abdominal wall of a human or animal body.

* * * * *